United States Patent [19]

Gratton et al.

[11] Patent Number: 5,213,105

[45] Date of Patent: May 25, 1993

[54] FREQUENCY DOMAIN OPTICAL IMAGING USING DIFFUSION OF INTENSITY MODULATED RADIATION

[75] Inventors: Enrico Gratton, Urbana; William W. Mantulin; Martin J. vandeVen, both of Champaign, all of Ill.

[73] Assignee: Research Corporation Technologies, Inc., Tucson, Ariz.

[21] Appl. No.: 624,385

[22] Filed: Dec. 4, 1990

[51] Int. Cl.$^5$ ............................................. A61B 8/00
[52] U.S. Cl. ................................. 128/664; 252/341; 128/665
[58] Field of Search ............................... 128/664–665

[56] References Cited

U.S. PATENT DOCUMENTS

| | | |
|---|---|---|
| 3,575,550 | 4/1971 | Korpel . |
| 3,716,659 | 2/1973 | Korpel . |
| 3,748,470 | 7/1973 | Barrett . |
| 3,848,096 | 11/1974 | Marko . |
| 3,860,821 | 1/1975 | Barrett . |
| 3,946,433 | 3/1976 | Kermisch . |
| 3,986,160 | 10/1976 | Turner . |
| 4,063,549 | 12/1977 | Beretsky et al. . |
| 4,079,421 | 3/1978 | Kermisch . |
| 4,179,936 | 12/1979 | Bennett et al. . |
| 4,265,126 | 5/1981 | Papadofrangakis et al. . |
| 4,326,252 | 4/1982 | Kohno et al. . |
| 4,456,982 | 6/1984 | Tournois . |
| 4,497,544 | 2/1985 | Mitchell et al. . |
| 4,530,076 | 7/1985 | Dwyer . |
| 4,557,386 | 12/1986 | Buckley et al. . |
| 4,584,475 | 4/1986 | Lao . |
| 4,595,954 | 6/1986 | Endo et al. . |
| 4,736,348 | 4/1988 | Bednarczyk . |
| 4,810,875 | 3/1989 | Wyatt ........................... 128/664 |
| 4,839,652 | 6/1989 | O'Donnell et al. . |
| 4,884,246 | 11/1989 | Heyser et al. . |
| 4,905,202 | 2/1990 | Robillard . |
| 5,007,428 | 4/1991 | Watmough ...................... 128/664 |

OTHER PUBLICATIONS

Chance et al., "Time-Resolved Spectroscopy of Hemoglobin and Myoglobin in Resting and Ischemic Muscle," Anal. Biochem. 174, 698–707 (1988).

(List continued on next page.)

Primary Examiner—Kyle L. Howell
Assistant Examiner—Robert L. Nasser, Jr.
Attorney, Agent, or Firm—Scully, Scott, Murphy & Presser

[57] ABSTRACT

Arrangements are disclosed for producing images based upon diffusional wave theory and frequency domain analysis. A medium to be imaged is illuminated with amplitude modulated radiation, and diffusional radiation transmitted or reflected by the medium is detected at a plurality of detection locations, as by a television camera. The phase and also the amplitude demodulation of the amplitude modulated diffusional radiation is detected at each detection location. A relative phase image and also a demodulation amplitude image of the medium are then generated from respectively the detected relative phase values and the detected demodulation amplitudes of the diffusional radiation at the plurality of locations. The present invention is particularly suited for medical applications for generating images of internal anatomical details of the body by using a near infrared amplitude modulated source for illumination of the body. In such medical applications, the body is illuminated with near infrared radiation having a wavelength between 600 and 1200 nanometers which is amplitude modulated at a frequency in the megahertz to gegihertz range, and internal images of the patient are generated for medical diagnosis. In preferred embodiments, a laser is utilized to generate the near infrared radiation near or below a 10 watt power level which is coupled by fiber optic cables to the body of the patient. Detection is also with fiber optic cables placed in direct contact with an opposed surface of the body which couple the transmitted diffusional radiation to an image intensifier placed in front of a television camera detector. The gain of the image intensifier is modulated at a frequency to obtain a heterodyned output frequency of less than 60 hertz which is within the detection bandwidth of the television camera.

36 Claims, 9 Drawing Sheets

OTHER PUBLICATIONS

Singer et al., "Image Reconstruction of the Interior of Bodies That Diffuse Radiation," Science 248, 990–993 (1990).

Nioka et al., "InVivo Continuous Noninvasive Measurement of Hemoglobin Saturation of Brain Tissue," Hematology and Oncology 773.

Chance et al., "New Techniques for Evaluating Metabolic Brain Injury in Newborn Infants," Critical Care Medicine 17, 465–471 (1989).

Spears et al., "Chrono-Coherent Imaging for Medicine," IEEE Engineering in Medicine and Biology Magazine, 21–23 (Dec. 1989).

Chance et al., "Comparison of Time-Resolved and -Unresolved Measurements of Deoxyhemoglobin in Brain," Proc. Natl. Acad. Sci. U.S.A. 85, 4971–4975 (1988).

Tamura et al., "The Simultaneous Measurements of Tissue Oxygen Concentration and Energy State by Near-Infrared and Nuclear Magnetic Resonance Spectroscopy," 359–363.

Chance, "Spectrophotometic Observations of Absorbance Changes in the Infrared Region in Suspensions of Mitochondria and in Submitochondrial Particles," Infrared Absorbance Changes in Mitochondria, 293–303.

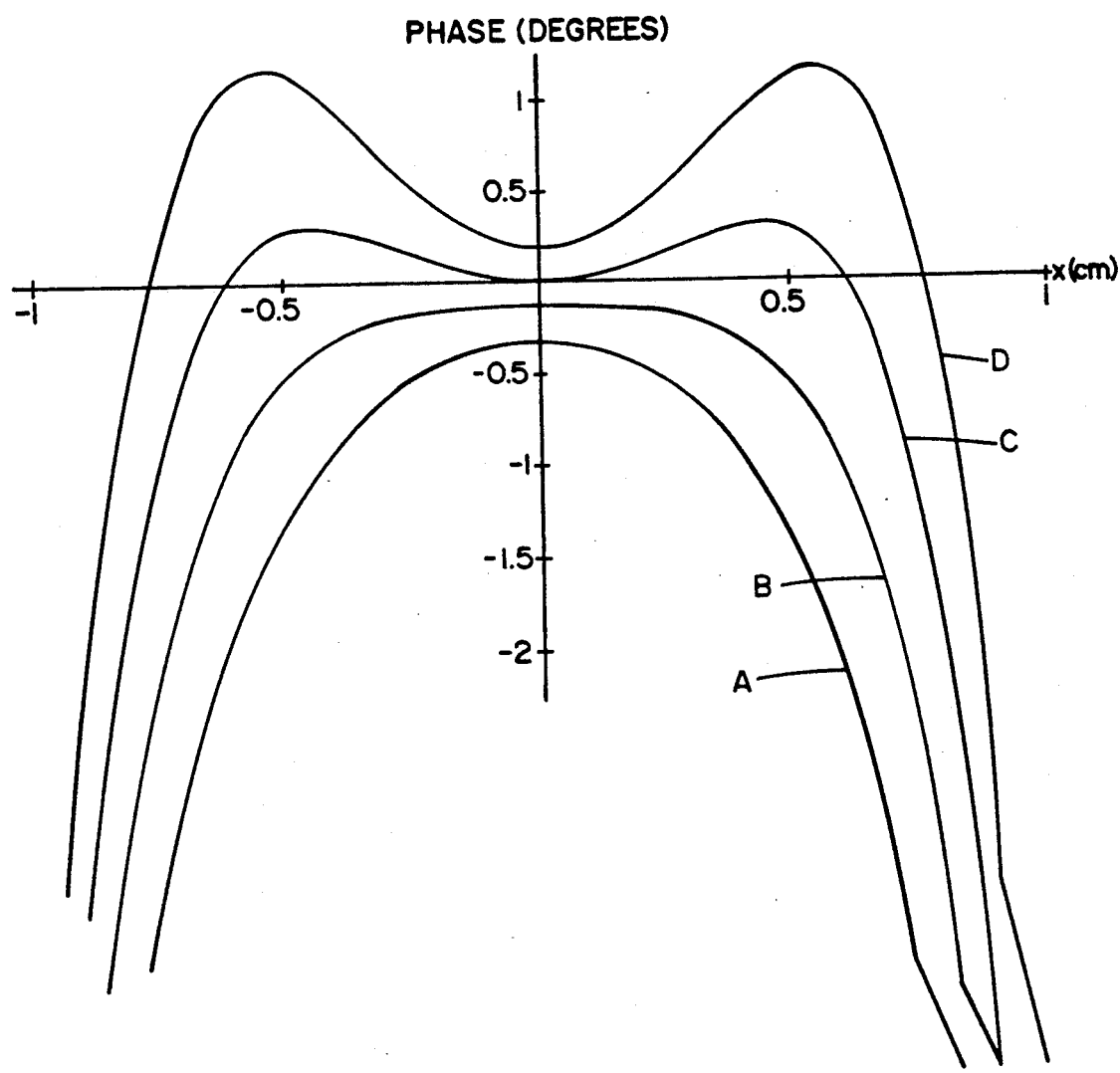
FIG. 3 (NOIS) α = 10⁶ cm²/sec  A: ω = 160 MHz;  B: ω = 180 MHz
C: ω = 200 MHz;  D: ω = 220 MHz

FREQUENCY DOMAIN OPTICAL IMAGING USING DIFFUSION OF INTENSITY MODULATED RADIATION

This invention was made with Government support under PR-03155 awarded by the National Institutes of Health. The Government has certain rights in the invention.

BACKGROUND OF THE INVENTION

1. Field of the Invention

The present invention relates generally to an arrangement, including a method and system, for producing images based upon diffusional wave theory and frequency domain analysis. A medium to be imaged is illuminated with amplitude modulated radiation, and radiation transmitted or reflected by the medium is detected at a plurality of detection locations, as by a television camera. The phase and also the amplitude demodulation of the radiation is detected, and a relative phase image and also a demodulation amplitude image of the medium are generated from respectively the detected relative phase values and the detected demodulation amplitudes of the radiation at the plurality of locations.

The present invention is particularly suited for medical applications for generating images of internal anatomical details of the body using a rear infrared amplitude modulated source for illumination and a television camera with a modulated image intensifier as a detector. In greater detail, the subject invention pertains to an arrangement as described which is capable of real-time imaging of thick tissues with a resolution of a few millimeters, and is based upon the physical mechanisms of photon migration in tissues with a particular focus on diffusional wave optics and frequency domain analysis.

2. Discussion of the Prior Art

Imaging of the interior of the human body is of paramount importance in medicine. Current methods are based upon x-rays, nuclear magnetic resonance, ultrasound and other specialized methods which noninvasively provide images of internal anatomical details. Optical imaging in the near infrared has been suggested as an attractive alternative method, Chance, B., et al. Anal. Biochem. 174, 698-707 (1988). However, prior efforts and studies have concentrated on the detection in the time domain of so-called "ballistic photons," i.e., those few photons which travel through the tissues with no scattering. The primary problem has been distinguishing ballistic photons from others which are subjected to several collisions.

Previous studies of coherent light propagation in tissues have concluded that the penetration depth for most animal tissues is generally a fraction cf a millimeter, and that a lack of optical coherence prevents the realization of optical imaging. Several approaches have been proposed to achieve optical image reconstruction of thick tissues (more than a centimeter), but all have met with a singular lack of success.

Patent application Ser. No. 310,404, filed Feb. 13, 1989, for "Method and Means for Parallel Frequency Acquisition in Frequency Domain Fluorometry" is also of interest to the present invention as it discloses an arrangement in which an image intensifier is utilized in association with a camera detector, and the gain of the image intensifier is modulated at an appropriate frequency to obtain a heterodyned output frequency within the bandwidth of the camera detector.

SUMMARY OF THE INVENTION

In accordance with the teachings herein, the present invention provides an arrangement for producing images based upon diffusional wave theory and frequency domain analysis. A medium to be imaged is illuminated with amplitude modulated radiation, and radiation transmitted or reflected by the media is detected at a plurality of detection locations, as by a television camera. The phase and also the amplitude demodulation of the amplitude modulated radiation is detected at each detection location. A relative phase image and also a demodulation amplitude image of the medium are then generated from respectively the detected relative phase values and the detected demodulation amplitudes of the radiation at the plurality of locations.

The present invention is particularly suited for medical applications for generating images of internal anatomical details of the body by using a near infrared amplitude modulated source for illumination of the body. In such medical applications, the body is illuminated with near infrared radiation having a wavelength between 600 and 1200 nanometers which is amplitude modulated at a frequency in the megahertz to gegihertz range, and internal images of the patient are generated for medical diagnosis. In preferred embodiments, a laser is utilized to generate the near infrared radiation near or below a 10 watt power level at a preferred wavelength between 680 and 850 nanometers, and is coupled by fiber optic cables to the body of the patient. Detection is also with fiber optic cables placed in direct contact with an opposed surface of the body which couple the transmitted radiation to an image intensifier placed in front of a television camera detector. The gain of the image intensifier is modulated at a frequency to obtain a heterodyned output frequency of less than 60 hertz which is within the detection bandwidth of the television camera. In one specialized embodiment, the detector arrangement can operate in a Doppler frequency shift mode to measure the flow rate of fluids such as blood in the patient.

In alternative embodiments, the phase and demodulation amplitude data is generated at different modulation frequencies and different illumination wavelengths, and a computer is programmed to produce false color representations, smoothing, filtering or contrast enhancement. In some embodiments, the detected phase and demodulation amplitude data can be stored in memory for subsequent processing by the computer.

The present invention can be used to perform optical imaging of solid and fluid objects in highly scattering media. The physical principle of operation is that light (or other suitable radiation) pulses entering the medium are scattered and/or absorbed, and the amplitude modulated light is phase shifted and demodulated by the medium. The wavefront of the amplitude modulated wave maintains coherence during its propagation through the medium, similar to the phenomenology of wave optics of scalar fields. After the wavefront passes through the medium, the phase shift and demodulation of the transmitted beam is detected with high precision ($\leq 0.1\%$).

The retardation of the wavefront by regions of effectively different phase velocities creates a shadow of the region(s) being imaged or visualized. The intensity profile alone does not provide the resolution available from the frequency domain approach.

Although preferred embodiments disclosed herein operate in a mode in which radiation transmitted through a medium is detected, two additional modes of operation are possible, a reflectance mode and a Doppler shift mode.

The present invention can be utilized to generate images in real time in fields which require real time analysis, such as during surgery and real time mapping of brain activity. Real time generation of images can be achieved with a fast detector such as a CCD camera preceded by an image intensifier operating with a computer of appropriate processing power.

Applications of the present invention have thus far focused on biomedical imaging of thick tissues which favor excitation sources operating in the near infrared, hence the acronym near infrared optical imaging system (NOIS). The requirements for imaging dictate that the medium being imaged be transparent to the excitation wavelength. In principle, the source of radiation is not restricted to light, and other sources such as pulsed neutron sources can be utilized in suitable applications.

In contrast to the prior art, the present invention employs the bulk of the photon flux which travels slowly (relative to its velocity in a vacuum) through body tissues which are optically dense media. The effective wavelength of the amplitude modulated light wave is greatly reduced because of the slow average propagation velocity through the body tissues. However, the smaller effective wavelength allows the imaging of small objects, with applications in the medical field where imaging of internal details of the body is of paramount importance.

Near infrared optical imaging provides images of anatomical features, and also yields information about metabolism. For example, one clinical application in a post radiation treatment scenario is the differentiation of necrotic tissues from tumor tissues based upon hemoglobin absorption.

The application of the present invention for imaging in the medical field are based upon the principle that near infrared light in the 600 to 1200 nm region, or more preferably the 680 to 850 nm region, is weakly absorbed by body tissues. The major absorbers are heme proteins and heme derivatives. The radiation is strongly scattered in the tissues and the effective path length can be very long. If radiation amplitude modulated at a frequency in the MHz-GHz range travels through the tissues, then because of multiple scattering, the radiation front migrates with a relatively low velocity. The effective wavelength of the amplitude modulated radiation is then greatly reduced, allowing images to be obtained with a resolution of a few millimeters.

The radiation source can be a laser or a laser diode or any other suitable source in the near infrared wavelength region which can be amplitude modulated or pulsed with harmonic content in the MHz-GHz region.

The detector can comprise a CCD or normal TV camera with an associated image intensifier. One function of the image intensifier is to modulate the gain of the detector system at a frequency which is very close to the frequency of modulation of the near infrared light. Using a frequency conversion process which takes place due to heterodyning of the light modulation frequency and the gain modulation of the image intensifier, the effective frequency seen by the detector can be very low, e.g., a few hertz. Camera type detectors can be read at a speed of 60 frames per second. If the converted frequency is well below 60 Hz, then the phase and amplitude demodulation data can be stored in memory, and then processed by a programmed computer to provide the locations of regions of different phase velocities and modulation depth. Using this approach, a map or image of the regions of higher absorption or transmittance can be obtained. The ability to produce images of the brain is particularly interesting where myoglobin is almost absent and hemoglobin is concentrated in well defined regions. Also, tumor regions, which contain relatively high blood concentration, can be imaged. The near infrared optical imaging system is noninvasive, and the required light intensity to obtain an image is small compared to tissue damaging intensities.

The near infrared optical imaging system of the present invention provides the following advantages:

It is noninvasive and painless with illumination and detection being by fiber optic cables placed in direct contact with the skin;

It is nondegrading to tissue as the total optical power on the skin surface illuminated by the fiber bundle is well below the level of tissue damage;

It provides rapid and on-line data such as by a portable instrument with a CRT screen displaying the image in real time. On-line imaging can be particularly useful during surgery where standard imaging methods are not feasible;

It provides imaging of hemoglobin rich or poor regions. There are many instances in which rapid determination of regions high in hemoglobin concentration is necessary, particularly in cerebral vascular accident conditions (either obstructions or hemorrhages). It is noted that the oxidation state of hemoglobin, which can be detected by the disclosed apparatus, is dependent upon the metabolic activity in the tissue;

It provides improved resolution. PET scanning methods have a resolution of 3 to 5 mm, but require elaborate facilities and special chemistry for particle emission and detection. The system of the present invention provides comparable spatial resolution of soft tissue in a facile fashion;

It should be low cost. NMR, PET, and other imaging techniques are expensive compared to the cost of the present system which should be on the order of $100–200 K.

BRIEF DESCRIPTION OF THE DRAWINGS

The foregoing objects and advantages of the present invention for frequency domain optical imaging using diffusion of intensity modulated radiation may be more readily understood by one skilled in the art with reference being had to the following detailed description of several preferred embodiments thereof, taken in conjunction with the accompanying drawings wherein like elements are designated by identical reference numerals throughout the several views, and in which:

FIG. 3 shows several graphs based upon simulations and equations herein which indicate that two sources positioned 1 cm apart and viewed from a distance of 5 cm appear as two separated point images at frequencies above 200 MHz;

FIG. 4a illustrates phase delay plotted as a function of frequency and also as a function of the distance between source and detector optical fibers for light at 720 nm, while

DETAILED DESCRIPTION OF THE DRAWINGS

Figure 1:
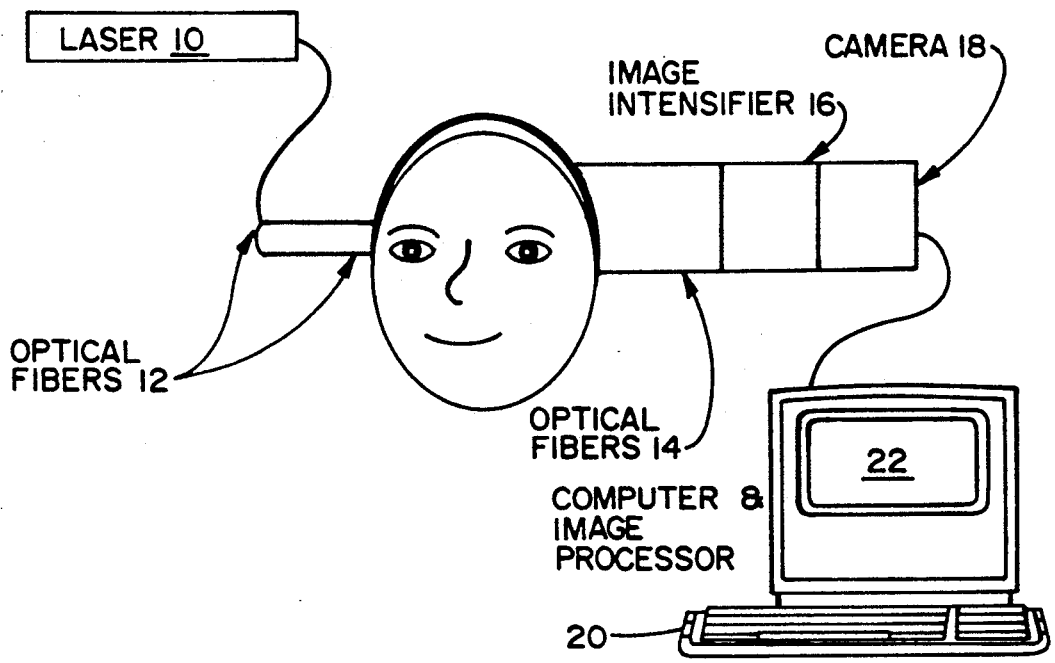
FIG. 1 illustrates a schematic representation of a near infrared optical imaging system pursuant to the teachings of the present invention, utilized to generate internal images of a patient's brain or other body parts.

The present invention is based upon studies of how a wavefront of amplitude modulated radiation such as light propagates through a highly scattering medium. It is specifically emphasized that it is only the wavefront of the amplitude modulated wave which is considered, not the optical field light front.

Diffusion and Diffusional Wave Optics

Light propagation in very turbid media can be mathematically treated as a diffusional process in which photons are particles undergoing a large number of collisions. The particle nature derives from the randomization of the electromagnetic wavefront after a few scattering events. The solution of the diffusion equation for amplitude modulated light propagating in a scattering medium is similar to the solution for heat diffusion in solids and can be better understood by the general theory of diffusional processes. Important aspects of propagation by diffusion are (1) diffusional waves can maintain coherence at large distances and (2) low frequencies propagate further than high frequencies. The operation of the present invention is based upon a solution of the diffusion equation for a point source at the origin), which is characterized by an average intensity $I_0$ and modulation M at frequency $\omega$.

$$I(r,t) = \frac{I_0}{r}(1 + Me^{[-r\sqrt{\omega/2\alpha}(1+i)+i(\omega t-\epsilon)]})$$

where r is the distance from the source in centimeters and $\alpha$ the photon diffusion constant in units of $cm^2/sec$. In the absence of an amplitude modulated signal ($\omega=0$) the solution corresponds to a spherical wave propagating without attenuation. The amplitude decays with the usual factor $1/r$, which simply implies the conservation of the number of photons. In the presence of diffusion, and for a non-zero frequency, the amplitude of the signal at a frequency $\omega$ decreases exponentially, and the light wavefront advances at constant velocity $$velocity = \sqrt{2\alpha\omega}$$

and has wavelength $$\lambda = 2\pi\sqrt{2\alpha/\omega}.$$

Resolution

Inspection of the above equation shows that higher modulation frequencies yield shorter wavelengths, and smaller diffusion constants also give shorter wavelengths. In principle, short wavelengths can be obtained using high frequency modulated waves in a very turbid medium. However, the amplitude of the modulated wave decreases exponentially with the same factors. Therefore the best resolution, i.e., the shortest wavelength, is obtained at the highest frequency with a measurable signal. The physical nature of the diffusional process limits the penetration depth at any given modulation frequency, because of the exponential decrease of the wave's amplitude. However, diffusion also decreases the velocity of light propagation. This phenomenon results in a reduced wavelength of the amplitude modulated wave with respect to the wavelength in a vacuum. Consequently diffusion causes enhanced resolution by an effective wavelength reduction. To assess the maximum resolution possible, a numerical example is presented for an ideal situation with negligible absorption. For a wavelength of 1 cm, the ratio $\omega/\alpha$ must satisfy the following equation.

$$\sqrt{\omega/2\alpha} = 2\pi/1 \text{ cm} = 6.28 \text{ cm}^{-1}$$

The amplitude of this wave decreases as exp $(-6.28r)$. For nondestructive testing, a reasonable maximum signal level is considered to be 10 W (equivalent to about $2 \cdot 10^{19}$ photons at 800 nm). Given the sensitivity of present day detectors, real time imaging tolerates an attenuation of a 10 W beam by a factor of $10^{14}$ to $10^{15}$. This order of magnitude calculation provides a limit of 5 cm for the maximum penetration of a wave of wavelength 1 cm.

Figure 2:
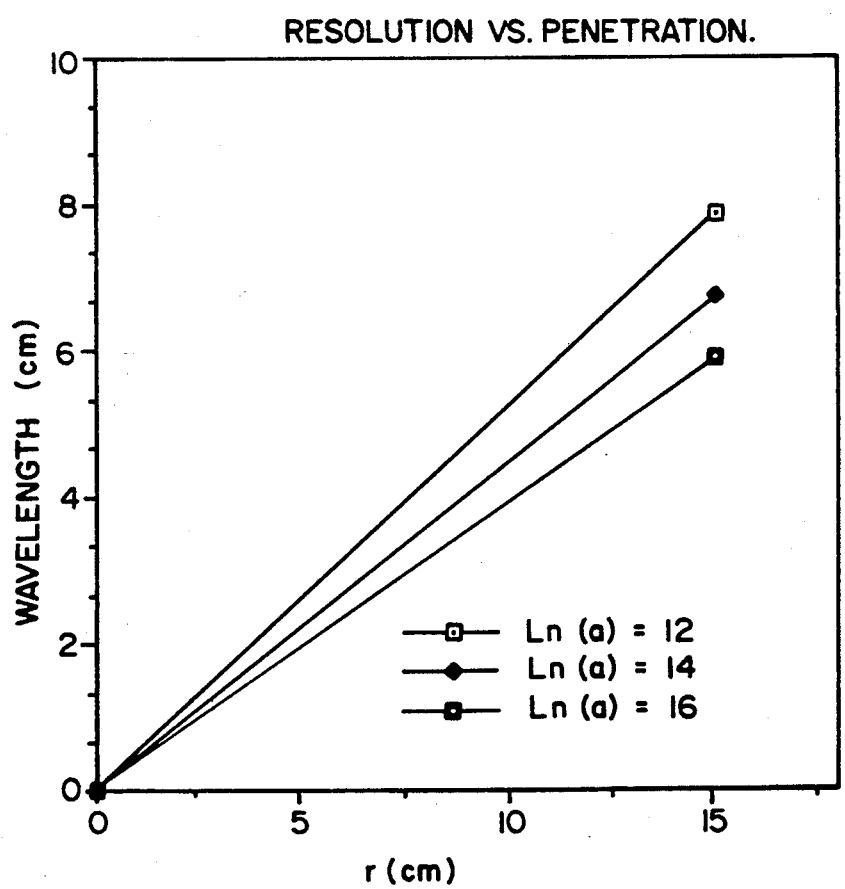
FIG. 2 illustrates several graphs of resolution of minimum wavelength plotted as a function of depth of penetration, based upon three different values of Ln(a)

FIG. 2 illustrates several graphs of resolution of minimum wavelength plotted as a function of depth of penetration, based upon three different values of Ln(a). In FIG. 2 the slope of the line is given by $$\lambda/r = 2\pi/ln(a)$$

where a is the maximum attenuation admissible by the particular experimental arrangement. Note that the larger the attenuation the better the resolution, but the improvement depends only logarithmically upon the attenuation. Inspection of the resolution chart of FIG. 2 shows that to achieve 10 cm of penetration, wavelengths larger than 2 cm must be used. For this special kind of diffusional wave optics, the resolution is not determined simply by the wavelength of the amplitude modulated wave. To illustrate this point, simulations have been performed using the above equations and assigning a value of $\alpha=10^6 cm^2/s$ and varying modulation frequencies from 160 to 220 MHz to achieve a penetration of about 5 cm.

FIG. 3 shows several graphs based upon simulations and equations herein which indicate that two sources positioned 1 cm apart and viewed from a distance of 5 cm appear as two separated points at frequencies above 200 MHz.

Contrast

In animal tissue, scattering is accompanied by absorption at the wavelength of the light source. In the wavelength region between 700 nm and 800 nm, where one embodiment of an instrument of the present invention operates, the major contributors to absorption are hemoglobin, myoglobin and other heme derivatives. If the absorbing material is uniformly distributed, the diffusion equation can be analytically solved. In the presence of absorption, with an absorption coefficient b (in units of sec$^{-1}$), and the same modulated point source used in the above equation, we obtain:

$$I(r,t) = \frac{I_0}{r} \{e^{-r\sqrt{b/a}} + Me^{-(rA(\omega)\cos B(\omega))} e^{-i(rA(\omega)\sin B(\omega) - \omega t + \epsilon)}\} \quad (1)$$

$$\text{with } \left(\frac{b^2 + \omega^2}{a^2}\right)^{1/4} = A(\omega) \text{ and } 1/2 \tan^{-1}(\omega/b) = B(\omega).$$

The presence of uniform absorption decreases the resolution by increasing the wavelength of the amplitude modulated wave. For localized absorption regions, the particular geometry of the light sinks must be included in the diffusion equation and a general closed solution cannot be written.

Diffusional Wave Optics in the Frequency Domain

The diffusional wave approach shows that amplitude modulated light waves in turbid media can be treated in the familiar framework of wave optics.

1. The superposition principle can be used to calculate the intensity at any given point from a number of point sources.
2. The photon intensity constitutes a scalar field, propagating at constant velocity in a spherical wave.
3. An effective index of refraction can be defined as the ratio of the velocity of the amplitude modulated wavefront to the velocity of light in a vacuum.
4. For diffusional waves, the propagation velocity depends upon the modulation frequency, but is independent of the distance from the source. The apparent index of refraction is also frequency dependent.

At any given modulation frequency, one recovers all the properties of wave optics of scalar fields. Therefore, in the frequency domain the measurement and analysis of light diffusing in tissues can be described using familiar concepts. For example, wave refraction occurs at a boundary between two different tissues. It causes a deviation of the direction of propagation of the wavefront, which is a function of the ratio of the phase velocities (apparent indices of refraction) in the two tissues. A major difference between normal light optics and diffusional wave optics is the exponential attenuation of the wave's amplitude as the wave propagates in the scattering medium. This phenomenon has similarities with light propagating in metals where absorption causes an exponential attenuation of the electric field at optical frequencies.

There is a practical difference in describing the diffusion of photons in the frequency domain with respect to its Fourier transform equivalent in the time domain. Namely, amplitude modulated waves propagate coherently, while pulses do not. This fact is crucial for image reconstruction. Furthermore, using well established frequency domain methods in conjunction with array detectors, it is possible to accurately measure, in real time, the average intensity, amplitude, and phase of the wavefront over a large area. Array detectors cannot be used with the pulse approach.

FIG. 1 illustrates a schematic representation of a near infrared optical imaging system pursuant to the teachings of the present invention, utilized to generate internal images of a patient's brain or other body parts. The optical imaging system includes a laser source 10 operating at an appropriate near infrared frequency, the output of which at approximately 10 watts is coupled through a bundle of optical fibers 12 to be transmitted through the patient's head and brain or other body parts. The transmitted radiation is picked up by a second bundle of optical fibers 14 and conducted thereby to an image intensifier 16 and then to a television camera detector 18, which can have a CCD type of detector. The output video signals of the television camera can be directed to a computer 20 for processing as described herein and display upon screen 22 or for storage in a memory in computer 20.

Frequency Domain Imaging Using Array Detectors

To obtain phase and modulation images of the light propagating in the tissue, it is necessary to use an array detector such as a CCD camera, in which the phase and modulation at each pixel is obtained. Since the light is modulated at frequencies of about 100 MHz, and since the camera reading frequency is approximately 60 Hz, at first it appears impossible to obtain information at 100 MHz. However, the inventors have recently shown that it is possible to use an image intensifier in front of the array detector and, by modulating the intensifier gain, obtain a frequency translation in the image intensifier from 100 MHz to well below 60 Hz, as disclosed in patent application Ser. No. 310,404, filed Feb. 13, 1989, for "Method and Means for Parallel Frequency Acquisition in Frequency Domain Fluorometry." This technique has been described and demonstrated (E. Gratton, B. Feddersen and M. vandeVen, Proc. SPIE "Time-Resolved Laser Spectroscopy in Biochemistry II" Jan. 14-19, 1990, Los Angeles, Calif.). At the detector level, the intensity at each pixel changes sinusoidally at low frequency. The intensity of each pixel can be rapidly and easily stored in the memory of the computer. By recording several different image frames in a period, the relative phase, modulation, and intensity can be obtained by simple calculations. For direct observation, the resulting phase and modulation map can be transformed into a phase and modulation image on the computer screen.

Image processing methods can be used to produce the actual image and enhance the contrast. The computer can be programmed with software to produce false color representations, smoothing, filtering or contrast enhancement, possibly in conjunction with detecting phase and modulation amplitude data at different modulation frequencies and different illumination wavelengths.

Figure 5:
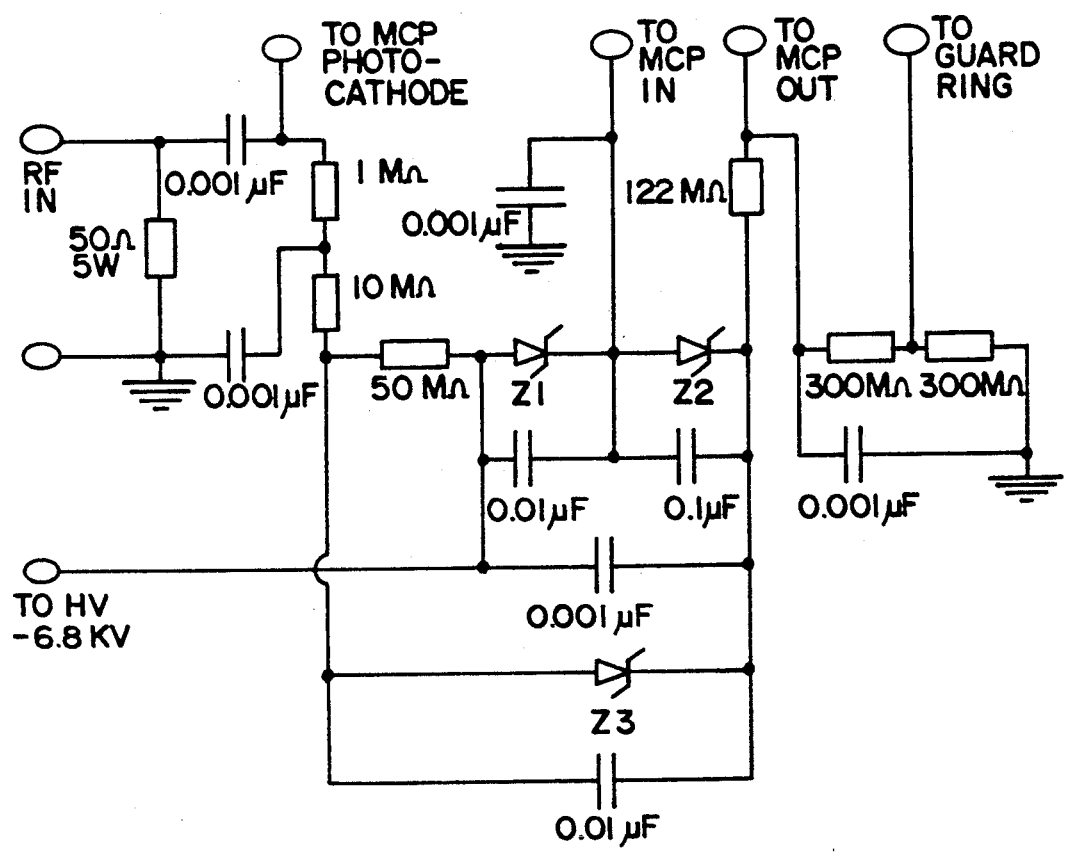
FIG. 5 is a schematic of a microchannel plate intensifier modulation circuit for an image intensifier to be placed in front of a camera detector, for modulating the gain of the image intensifier at a frequency to obtain a heterodyned output frequency of less than 60 hertz within the bandwidth of the camera.

FIG. 5 illustrates an electronic circuit used for 100 MHz modulation of a microchannel plate image intensifier (Mfg: Princeton Instruments, Inc., OMA detector model IRY512 G/RB). A 100 MHz heterodyning frequency is injected at the microchannel plate electrode. During operation of the microchannel plate intensifier modulation circuit of FIG. 5, the value of the bias voltage at the MCP In is obtained using Zener diodes Z1 and Z2. The radiofrequency signal is applied to the RFIN electrode. An alternate voltage of approximately 55 V peak to peak is applied at the RF unit. Approximately 80% modulation depth can be obtained. At frequencies up to 100 MHz, the intensifier view field is homogeneously modulated with modulation depth of about 80%.

Figure 6:
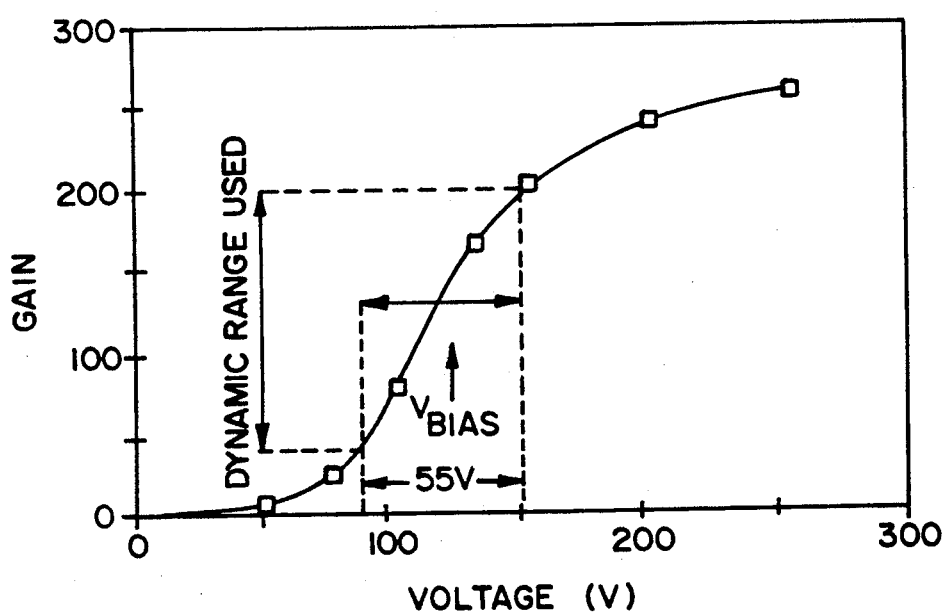
FIG. 6 illustrates a graph of the gain modulation of the microchannel plate image intensifier plotted as a function of voltage applied to the modulating electrode.

FIG. 6 illustrates the intensifier gain as a function of the voltage applied to the modulating electrode.

The microchannel plate image intensifier was used in conjunction with a diode array detector, or could use a similar image intensifier with a CCD image detector. A feature of a wave cross-correlation detection arrangement is the extremely small bandwidth of the filter, detector, which is about 1 Hz for the entire frequency range. At 100 MHz, a deviation of 1 Hz will produce a signal which is out of the filter bandwidth. This feature can be used to detect movements of fluids or tissues due to the Doppler effect. Since the effective light velocity in the highly scattering medium is on the order of $10^8$ cm/s, a velocity of 1 cm/s will Doppler shift the frequency of the modulated wave by about 1 Hz, which is a measurable amount. Velocities of 1 cm/s are typical for revealing body fluids and muscle condition.

Construction of the Real-Time Imaging Device

Figure 10:
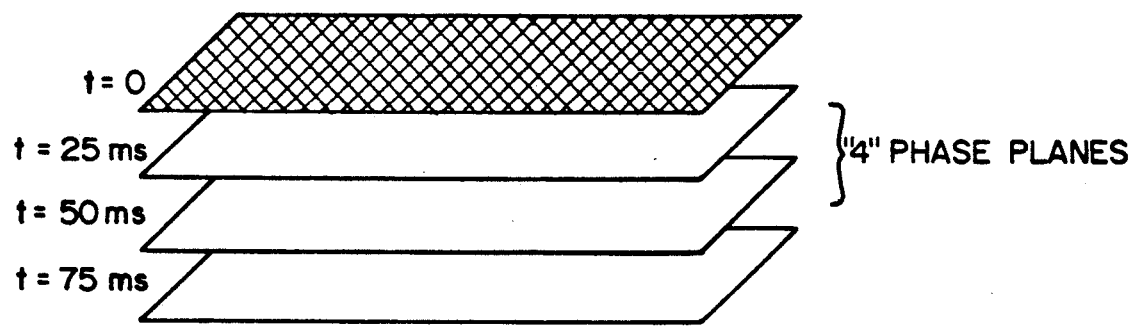
FIG. 10 illustrates schematically a process for utilizing four values of the detected intensity of radiation per each period of the intensity modulation radiation.

As provided by the manufacturer, a gated camera system, CCD F144, from ITT, Fort Wayne, Ind., had no provision for direct radio frequency modulation, and accordingly had to be modified. The camera is preferably connected to a fast frame grabber, preferably capable of real-time averaging. Since the system is utilizing a nonconventional operation mode, the synchronization circuit must be modified and the frame grabber programmed to switch between different image-phase planes. Per period, frame averaging can be performed in real-time to accumulate a reasonable signal in four "phase planes". The design of the camera circuit and synchronization electronics provide a method to measure, at each pixel, the amplitude and phase of the intensity modulated light. This can be performed by storing in a computer memory four values of the intensity per each period of the wave. FIG. 10 illustrates schematically this process for a wave of 10 Hz that has a period of 0.1 seconds. The entire frame is grabbed four times during this period ie. every 25 ms. At 100 ms, the grabbed frame is added to the previous frame at t=0 and the process is continued until a desired integration is reached, for example, the process is repeated 10 times for a total integration of 1 second.

The content of the four phase planes is transferred to a different memory location for processing and display while the acquisition process is again progressing in the background. Given the four phase planes, the value of the intensity, phase and modulation of the wave at 10 Hz can be calculated by using the following expressions (x,y indicate the pixel at position x and y)

$$\text{Intensity} = 1/4(I_{xy}(1) + I_{xy}(2) + I_{xy}(3) + I_{xy}(4))$$

$$\text{Phase} = \tan^{-1}\left(\frac{I_{xy}(1) - I_{xy}(3)}{I_{xy}(2) - I_{xy}(4)}\right)$$

-continued $$\text{Amplitude} = \sqrt{[I_{xy}(2) - I_{xy}(4)]^2 + [I_{xy}(1) - I_{xy}(3)]^2}$$

$$\text{Modulation} = \frac{\text{amplitude}}{\text{intensity}}$$

Of course, more than four planes can be acquired. For example, if eight planes are acquired, then it is possible to calculate the intensity, phase and amplitude of the second harmonics at 20 Hz. This process can continue for higher harmonics. Alternatively, when a large number of planes are acquired, the fast Fourier transform algorithm can be used instead of the above expressions.

The camera must also be optically interfaced with the large fiber optic bundle 14 placed adjacent to the tissue area where the light is collected. Due to cost considerations, a rigid glass bundle with a termination ratio of 1:5 is preferably used. The bundle is specifically designed to match the camera aperture or the other side. The end in contact with the tissue covers an area of approximately 5 cm×5 cm.

Regarding various arrangements for illumination, a small fiber can be used to produce a point source from which a spherical wave propagates in the tissue. Another arrangement could use plane wave illumination, which requires interfacing of the laser source with an illumination optical fiber bundle such as 12 which allows the use of greater laser power since the illuminated area is larger. Total light intensity is an important consideration in relation to real-time imaging and improves the penetration depth. One of the objectives of optical imaging is to obtain 3-D images of the internal tissues. The optical image method, contrary to other techniques, such as NMR, which produces 2-D slices, provides a 2-D projection of the diffusional light wavefront. One relatively simple method to obtain a 3-D image is to obtain more than one projection at different angles.

Computer Image Processing

The intensity image, as viewed from the camera viewfinder, has very little information. The phase and modulation images, which carry the information, can be imaged on the computer screen only after computer processing. In this sense, the computer is an integral part of the near infrared optical imaging system. For every pixel, phase, modulation, and intensity can be acquired at different modulation frequencies and different laser excitation wavelengths. This information can be displayed in different windows on the computer screen and manipulated by software to produce images using false color representations, smoothing, filtering, contrast enhancement, etc.

Preliminary Results

Several aspects of diffusional wave propagation discussed in the previous section have been experimentally confirmed. The experimental arrangement included a mode-locked Neodymium YAG laser (Antares, model 76S-ML-SHG), which synchronously pumps a rhodamine 6G dye laser. Most of the earlier experiments were performed using 620 nm excitation (instead of 700–800 nm) and modulation frequencies from 20–400 MHz. The exciting light was sent through a fiber optic bundle to a vessel containing an Intralipid suspension with an equivalent optical turbidity of about 10 in an optical path of 1 cm. The light was collected through a similar fiber optic bundle and conveyed to the detector of a frequency-domain fluorometer. The distance from source to detector was varied between 2 and 6 cm. Cross-correlation electronics were used to process the light signals.

Figure 4A:
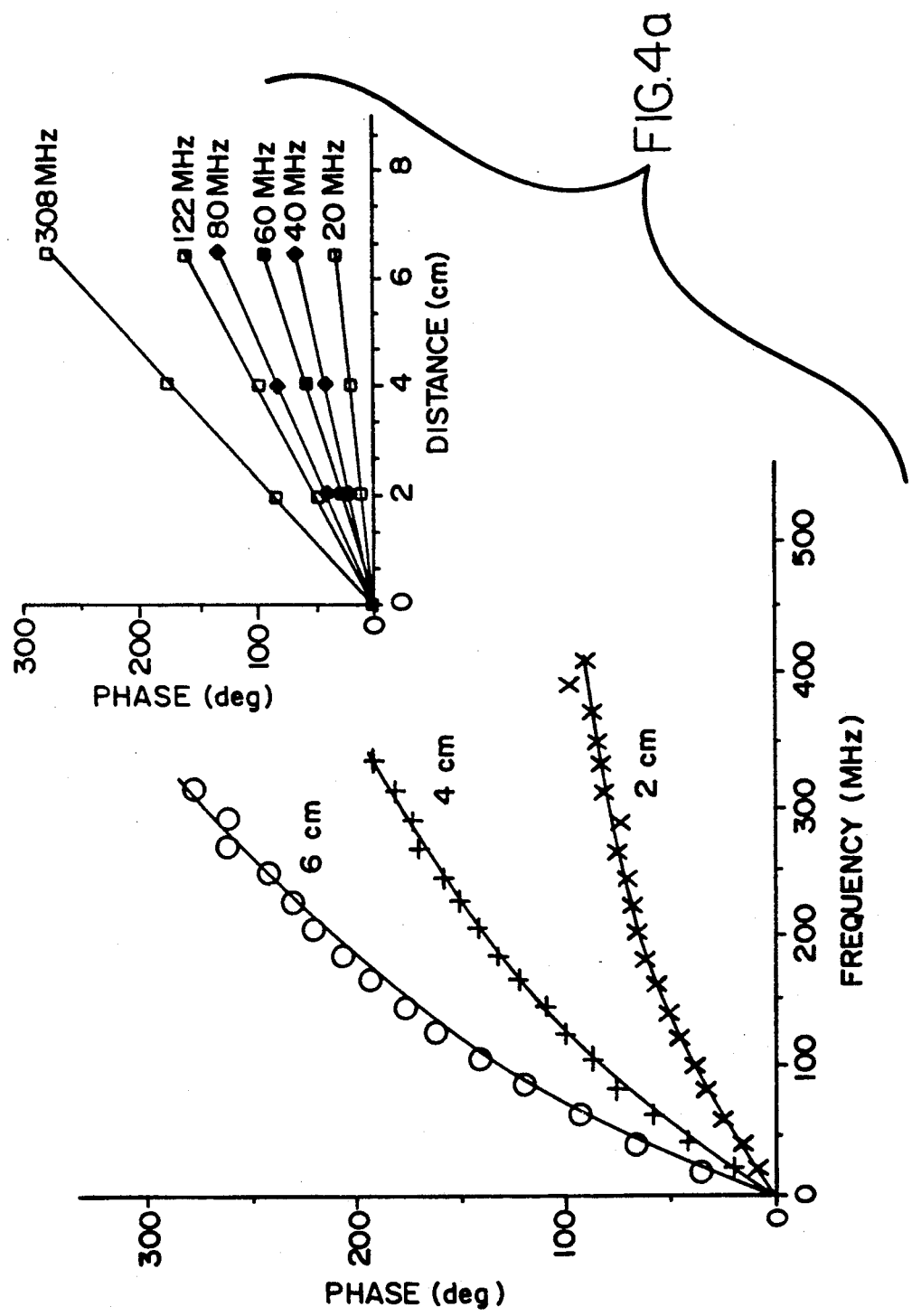
Figure 4B:
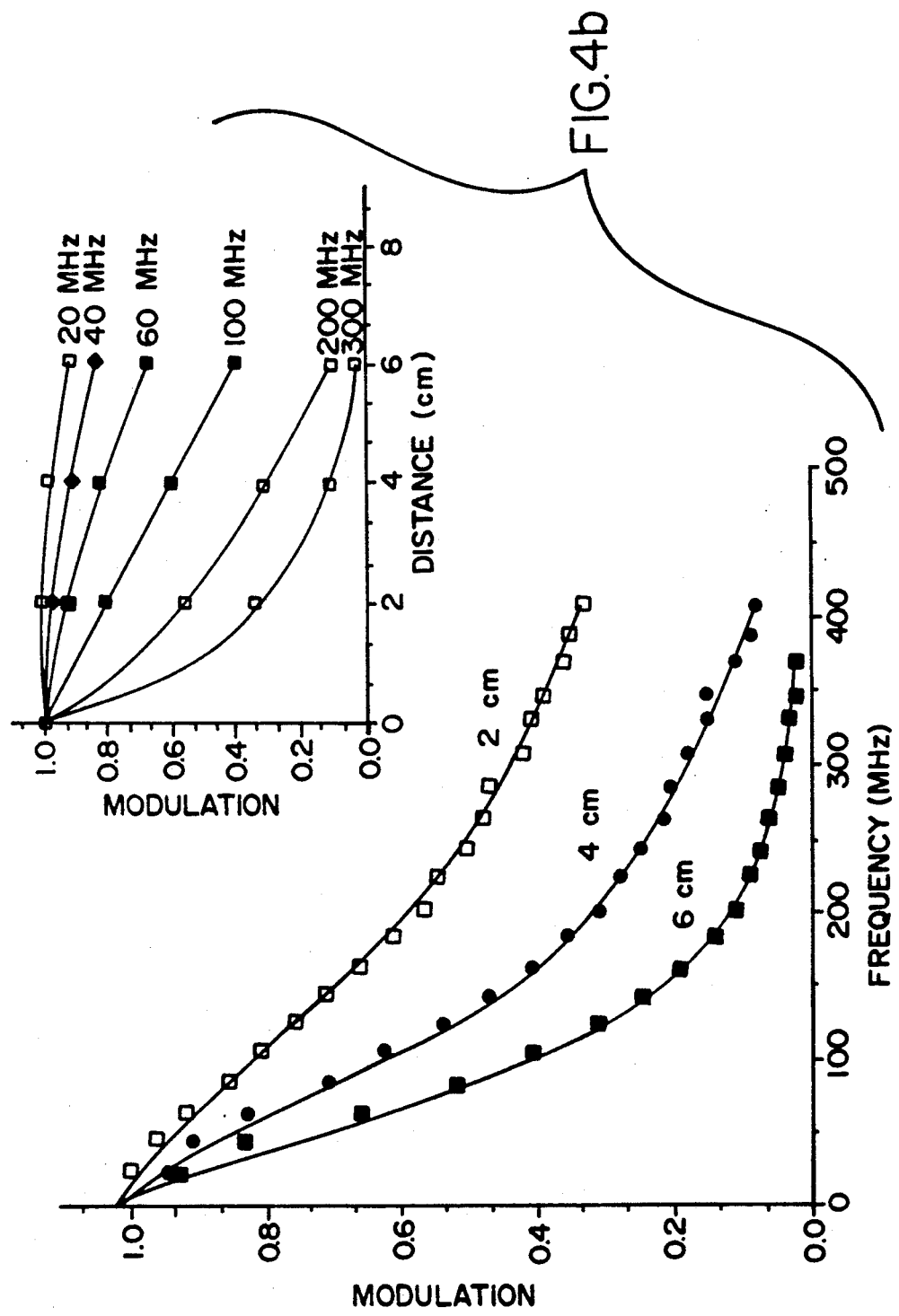
FIG. 4b illustrates modulation as a function of frequency and also as a function of the distance between source and detector optical fibers for light at 720 nm.

FIG. 4a illustrates phase delay plotted as a function of frequency and also as a function of the distance between source and detector optical fibers for light at 720 nm. The solid lines in FIG. 4 correspond to the fit using equation 1. All curves, including phase and modulation data, are fit using a single variable parameter $\alpha$, the photon diffusion coefficient. The agreement between experiment and the prediction based upon the diffusional model is excellent. To further test the validity of the developed equations, a small amount of an absorbing substance (black ink) was added to the Intralipid suspension. The medium was a suspension of 150 ml of 20% Intralipid suspension in 2850 ml of water. The O.D. due to turbidity was about 3 for a path length of 1 cm measured at 720 nm. The fibers were pointing to the bottom of the container and the distance between their ends was varied from 2 to 6 cm. Again the agreement between experimental data and the equation for diffusion in the presence of absorption is excellent. The data was fit in the presence of absorption using only one additional parameter b and employing the same value of $\alpha$ determined in the previous experiment.

For the experiments in simple isotropic scattering suspensions, full agreement was found between the diffusional model and the results. This observation is quite surprising since previous measurements using the time-domain method have disregarded the diffusional model as the correct framework to describe photon migration in tissues. In previous work, the solution of the diffusion equation for photons in the simple form given in equation 1 was not found. Since the image reconstruction approach is based upon the supposition of a framework for describing the photon diffusion process, it was crucial that some unusual and paradoxical predictions of the diffusional wave model be tested. Simple experiments were performed to demonstrate some crucial aspects of diffusional wave optics, (1) Interference between two different emitting sources, and (2) Refocusing a divergent diffusional wave using a lens. These two experiments are a natural consequence of the wave nature of diffusional light waves generated by an amplitude modulated source and lay the basis for a mathematical description of how the image is formed in more complicated cases, such as animal tissues.

Examples of Phase and Modulation Images of Simple Objects Immersed in Intralipid Suspension The phase and modulation map was measured of some simple objects at a spherical surface at a distance of about 10 cm from the source.

1. In the absence of objects, the phase and amplitude is constant over the entire spherical surface as predicted by the spherical wave solution of the diffusion equation.

2. When objects are interposed between the source and the observation spherical surface, at the optical shadow of the objects, there is an increase of the phase delay and a decrease of the amplitude value. The intensity value changes very little in the region of the optical shadow predicted by the diffusional wave optics. The increased phase delay and decreased modulation amplitude can be explained on the basis of a lengthening of the optical path of photons arriving at the region of the optical shadow. The phase is longer because the diffusional wave takes more time to arrive at the spherical surface, and the modulation amplitude has decreased because of the exponential attenuation of the wave that has traveled a longer distance. The phase and modulation map clearly reveals the presence of objects, while the intensity map is only marginally affected. The behavior of the phase and modulation amplitude can be qualitatively predicted, depending upon the properties of the intervening medium. For the discussion below, the transmission geometry is assumed and that the object being observed is in the optical shadow.

a) A completely opaque region will cause an increase in plane delay, a decrease of the modulation amplitude, and a small decrease in the intensity;

b) A higher scattering region with no absorption produces an increased phase delay and a modulation amplitude decrease; the intensity is not affected.

c) A partially absorbing region with no change in scattering causes an advance of the phase, an increase in the modulation amplitude, and a decrease of the intensity.

|  | Intensity | Phase | Modulation |
|---|---|---|---|
| Opaque | − | + | − |
| Scatter | − | + | − |
| Absorbancy/Uniformity | −/− | − | + | d) At relatively low modulation frequencies, if there is uniform absorption, there is virtually no demodulation. Instead, pure scattering gives strong demodulation.

e) The absorption depends upon the color or wavelength of the laser beam. By changing the laser wavelength, it is possible to explore different tissues and localize different substances in the tissue. At every pixel of the spherical projection surface, five different quantities can be measured or varied; intensity, phase, modulation amplitude, modulation frequency, and color of the light.

By proper selection and combination of these five quantities, detailed information can be obtained about the nature of the tissue through which the light has traveled. For example, it is possible to separately identify:

1. a locally opaque region;
2. a uniformly absorbing region;
3. a uniformly scattering region;
4. the nature of the absorbing substance through its absorption characteristics.

Experiments performed to date have used a transmission geometry and also a reflectance geometry.

Figure 7:
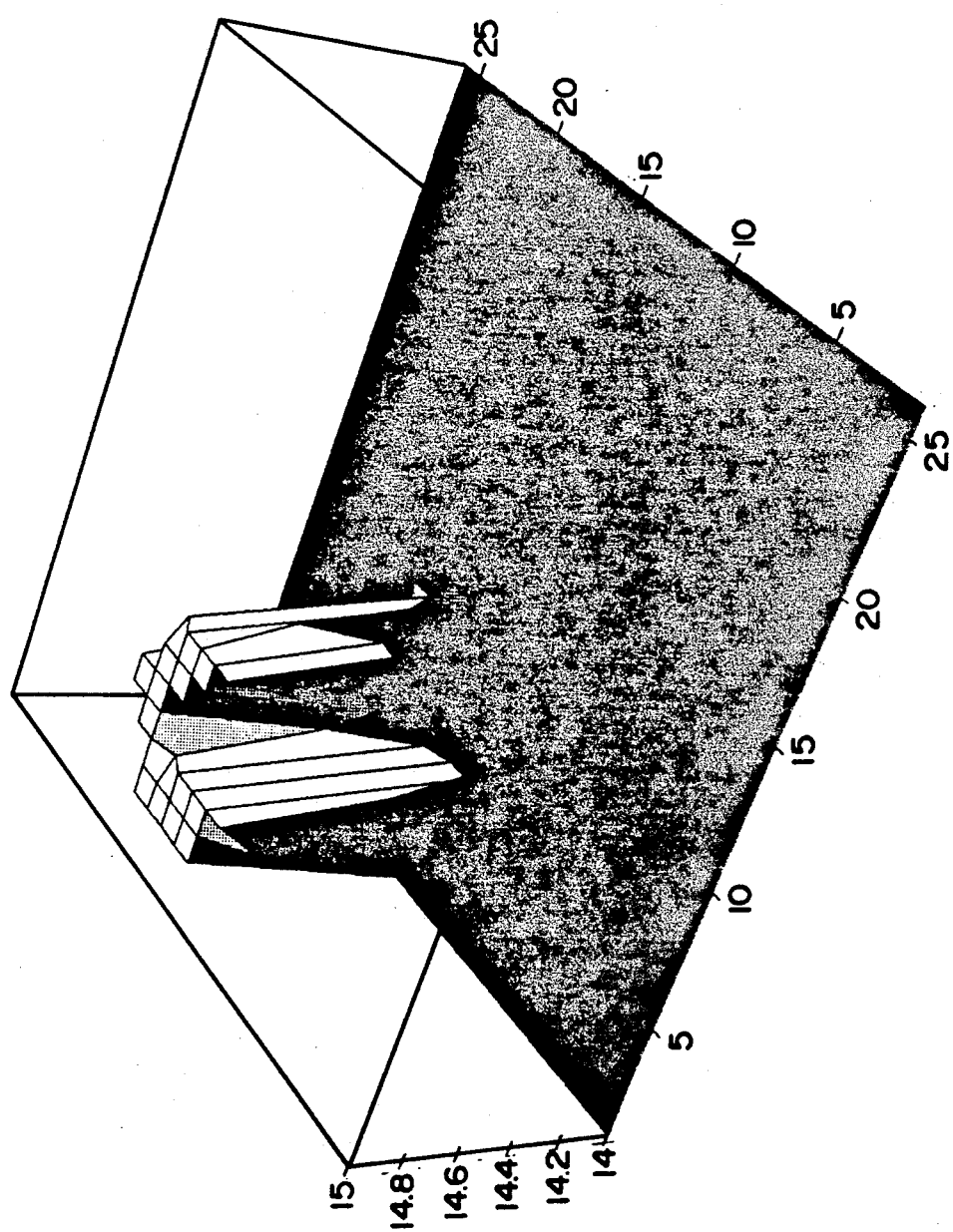
FIG. 7 illustrates the enhanced phase profile of an 18 mm washer.

Using the near-infrared optical imaging system, two-dimensional optical imaging of small objects and tissues has been achieved with a frequency domain fluorometer coupled to a single detector. Specifically, intensity, phase shift and modulation values were generated for an 18 mm washer, and were used to produce an enhanced phase profile as shown in FIG. 7, and the following which are not illustrated, two separated nuts, and a foreign object in the brain. The preliminary 2-D figures were produced with a software package Mathematica, which provides a tool for amplifying and manipulating the images, run on a personal computer. The physical process underlying the success in producing optical images is the coherent propagation of amplitude modulated waves. Consequently, the intensity, phase and modulation images of the projecting wavefront are well defined and with complementary information. This level of structural detail proves that the NOIS technique of the present invention provides the high spatial resolution necessary for clinical applications.

Figure 8:
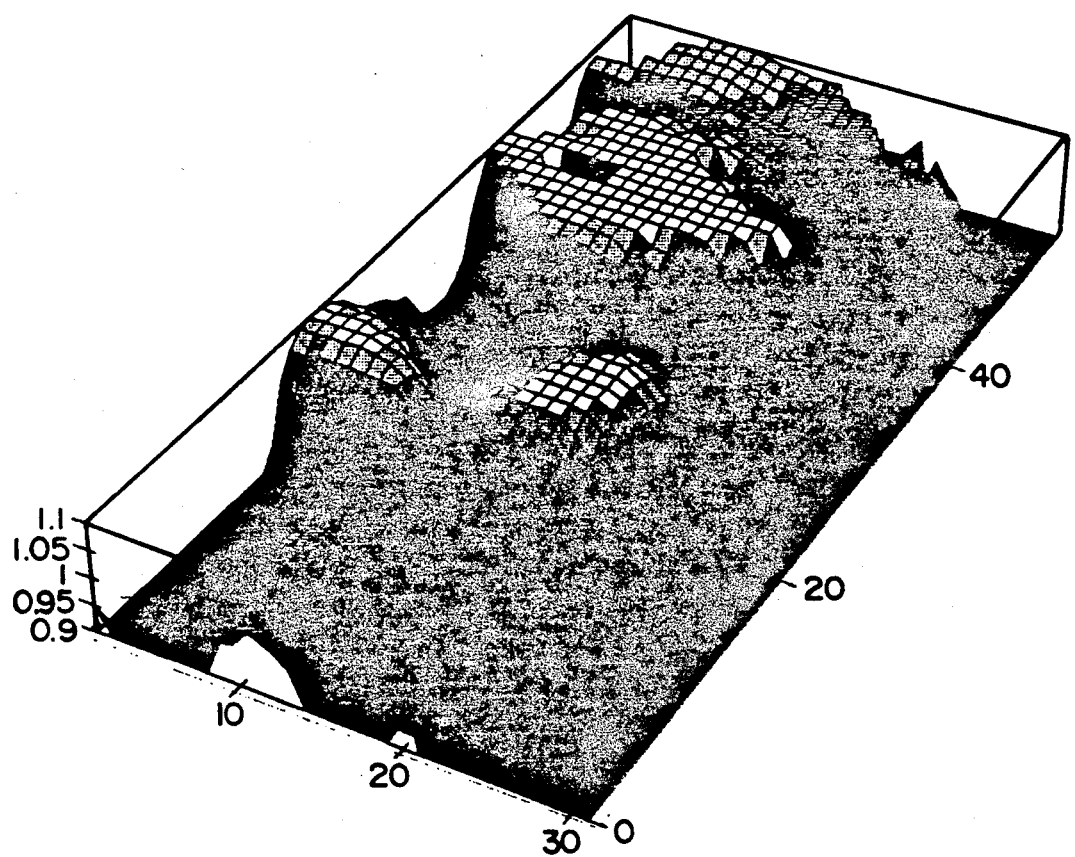
FIGS. 8 and 9 are respectively a phase profile image and a modulation profile image obtained for a mouse.
Figure 9:
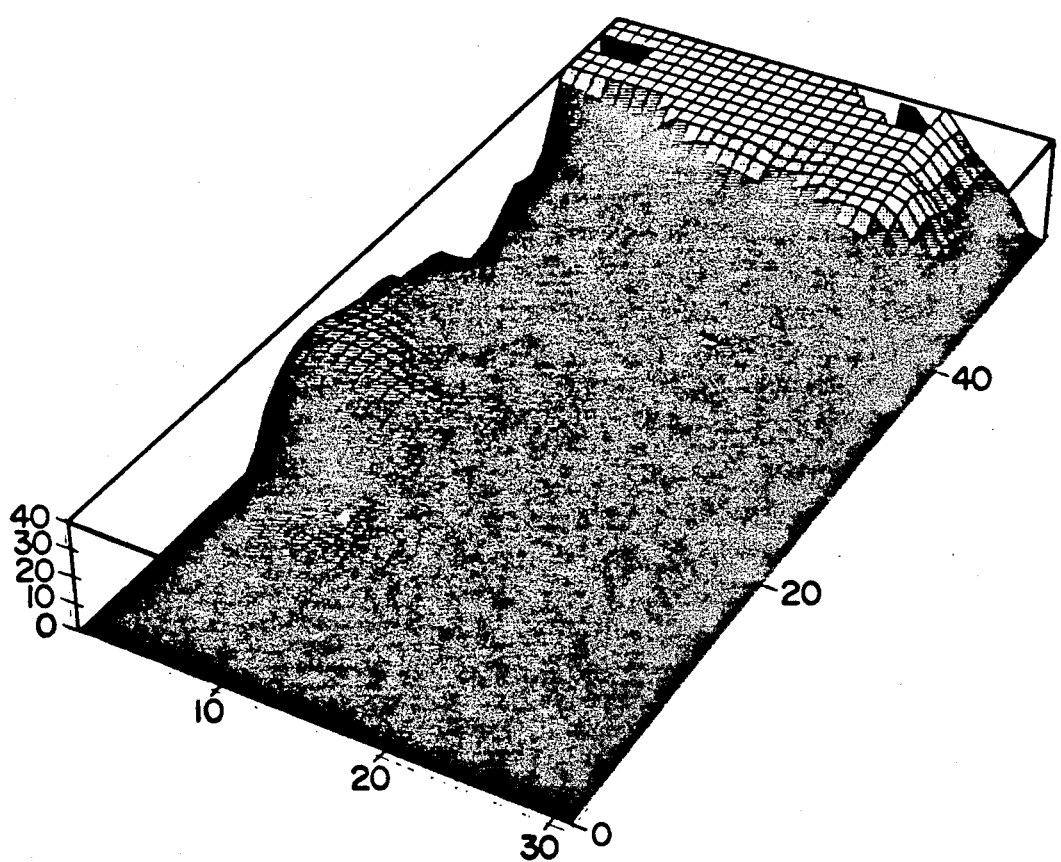

FIGS. 8 and 9 illustrate respectively a phase profile image and modulation profile image obtained for a small female mouse. FIG. 8 is actually the superposition of two x-y scans covering the front and hind sections. The reproducibility of the scan is so precise that a seam is not evident in the image reconstruction. The head and the brain are to the left of the image and the lungs, heart and abdomen appear as one traverses the image. The dark low amplitude region corresponds to the contrasting intralipid suspension. The head of the mouse is very clear in the foreground (x,y coordinates 5,10). In the modulation image of FIG. 9, the hind leg of the mouse is clearly visible at x,y coordinates 45,25.

In summary, the data clearly demonstrates that optical imaging of objects and tissues and intensity signals provide varied and complementary information about the region under observation. Additional contrast to the amplitude modulated signal can be provided by excitation wavelength manipulation to regions of higher or lower absorbance. The basic data was generated using an x-y raster scan for spatial discrimination, and in alternative embodiments a camera and imaging processing system can be used instead.

Two other variations of the optical imaging method are possible, reflectance and Doppler shift approaches. In the reflectance geometry mode, the diffusional waves that propagate along different paths exhibit different amplitudes at the recombination point. In the Doppler shift method the coherence of the diffusional wavefront can be utilized to detect movements or flow of fluids. In the disclosed transmission mode embodiment, the filters select a frequency bandwidth of 1 Hz, compared to a modulation frequency of 100-200 MHz.

Figure 11:
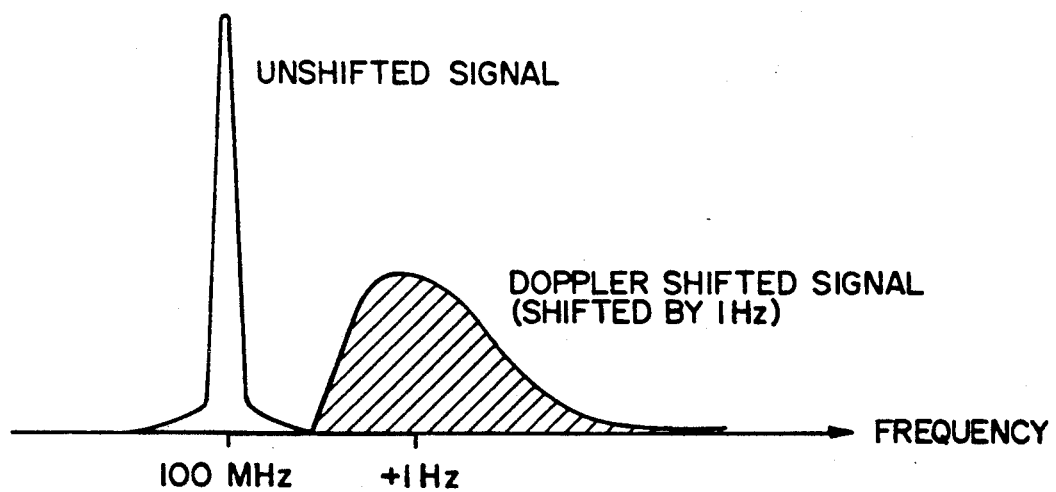
FIG. 11 illustrates, in association with a Doppler shifted frequency mode of operation, a Doppler shifted frequency signal appearing as an "out of band" signal.

The filter bandwidth is determined by the integration time, which in the example given herein is 1 second, but it can be made much narrower by increasing the integration time; for example, the filter will have a bandwidth of approximately 0.1 Hz for an integration time of 10 seconds. A Doppler shifted frequency will appear as an "out of band" signal as illustrated schematically in FIG. 11. The Doppler shifted signal can be detected by a spectral analysis of the signal, which can be easily obtained with a computer program that moves to the cross-correlation frequency by small increments. Given that diffusion rates are on the order of 1 cm/sec and velocity of the light front is $10^8$ cm/sec in the highly scattering medium, the resultant Doppler shift is about 1 Hz, namely the resolution of our filters. Such a Doppler signal is resolvable with current instrumental capabilities since it is outside the bandwidth of our filters.

Real time (video rate) imaging utilizing a CCD camera with an image intensifier and a computer can allow real time images of an observational area. The speed of processing is one of the major benefits of optical imaging. Examples of fields that require speed are visualization during surgery and real time mapping of brain activity.

The field of biomedical imaging of thick tissues has dictated excitation sources operating in the near infrared. The requirements for imaging dictate that the material be transparent to the excitation wavelength, noting that scattering does not preclude operation. Imaging of composite materials, such as rigid plastics impregnated with (graphite) fibers, should be appropriate candidates, assuming the selection of proper laser source. Moreover, in principle the source of wave energy is rot restricted to lasers, and other sources such as pulsed neutron sources or other forms of wave energy may find application in other technological areas in the detection of coherent wave fronts for imaging purposes.

While several embodiments and variations of the present invention for frequency domain optical imaging using diffusion of intensity modulated radiation are described in detail herein, it should be apparent that the disclosure and teachings of the present invention will suggest many alternative designs to those skilled in the art.

What is claimed is:

1. A method for producing images based upon diffusion of intensity modulated radiation and frequency domain analysis comprising:
   a. illuminating a medium with light radiation which is amplitude modulated;
   b. detecting amplitude modulated diffusional radiation from the medium at a plurality of detection locations forming a detection area, including detecting the phase of the amplitude modulated diffusional radiation at each detection location, and detecting the demodulation of the amplitude modulated diffusional radiation at each detection location; and
   c. displaying an image of the medium comprised of data from the detected relative phase or demodulation of the amplitude modulated diffusional radiation at each detection location.

2. A method for producing images based upon diffusion of intensity modulated radiation and frequency domain analysis as claimed in claim 1, wherein said amplitude modulation is at a frequency in the megahertz to gegihertz range.

3. A method for producing images based upon diffusion of intensity modulated radiation and frequency domain analysis as claimed in claim 2, including illuminating a patient with near infrared radiation having a wavelength between 600 and 1200 nanometers, amplitude modulating the radiation at a frequency in the megahertz to gegihertz range, and displaying internal images of the patient for medical diagnosis.

4. A method for producing images based upon diffusion of intensity modulated radiation and frequency domain analysis as claimed in claim 3, said illuminating step including utilizing a laser to generate near infrared radiation having a wavelength between 680 and 850 nanometers.

5. A method for producing images based upon diffusion of intensity modulated radiation and frequency domain analysis as claimed in claim 3, wherein said illuminating step is with fiber optic cables placed in direct contact with the body of the patient.

6. A method for producing images based upon diffusion of intensity modulated radiation and frequency domain analysis as claimed in claim 5, wherein said detecting step is with fiber optic cables placed in direct contact with the body of the patient.

7. A method for producing images based upon diffusion of intensity modulated radiation and frequency domain analysis as claimed in claim 3, wherein said detecting step is with a camera type detector.

8. A method for producing images based upon diffusion of intensity modulated radiation and frequency domain analysis as claimed in claim 7, including an image intensifier in front of the camera detector, and modulating the gain of the image intensifier at a frequency to obtain a heterodyned output frequency for the camera detector of less than 60 hertz.

9. A method for producing images based upon diffusion of intensity modulated radiation and frequency domain analysis as claimed in claim 3, wherein said illuminating step is below 10 watt power level.

10. A method for producing images based upon diffusion of intensity modulated radiation and frequency domain analysis as claimed in claim 3, further including utilizing a Doppler frequency shift mode to measure the flow rate of fluids in the patient.

11. A method for producing images based upon diffusion of intensity modulated radiation and frequency domain analysis as claimed in claim 1, wherein said step of displaying includes:
   a. displaying a relative phase image of the medium comprised of the detected relative phase values of the diffusional radiation at the plurality of detection locations; and
   b. displaying a demodulation amplitude image of the medium comprised of the detected demodulation amplitudes of the diffusional radiation at the plurality of detection locations.

12. A method for producing images based upon diffusion of intensity modulated radiation and frequency domain analysis as claimed in claim 1, including detecting phase and modulation amplitude data at different modulation frequencies and different illumination wavelengths, and utilizing a computer programmed to produce false color representations, smoothing, filtering or contrast enhancement.

13. A method for producing images based upon diffusion of intensity modulated radiation and frequency domain analysis as claimed in claim 1, including the step of storing in memory the detected phase and modulation amplitude data.

14. A method for producing images based upon diffusion of intensity modulated radiation and frequency domain analysis as claimed in claim 1, wherein said step of detecting comprises detecting diffusional radiation transmitted by the media.

15. A method for producing images based upon diffusion of intensity modulated radiation and frequency domain analysis as claimed in claim 1, wherein said step of detecting comprises detecting diffusional radiation reflected by the media.

16. A method for producing images based upon diffusion of intensity modulated radiation and frequency domain analysis as claimed in claim 1, wherein said step of illuminating is with a pulsed neutron source.

17. A method for producing images based upon diffusion of intensity modulated radiation and frequency domain analysis as claimed in claim 1, wherein said detecting step comprises detecting radiation with a camera and wherein each detection location comprises a pixel of the camera detector.

18. A method for producing images based upon diffusion of intensity modulated radiation and frequency domain analysis as claimed in claim 1, wherein said illuminating step comprises illuminating the medium with light which is amplitude modulated.

19. A system for producing images based upon diffusion of intensity modulated radiation and frequency domain analysis comprising:
   a. means for illuminating a medium with light radiation which is amplitude modulated;
   b. means for detecting amplitude modulated diffusional radiation from the medium at a plurality of detection locations forming a detection area, including means for detecting the phase of the amplitude modulated diffusional radiation at each detection location, and means for detecting the demodulation of the amplitude modulated diffusional radiation at each detection location; and
   c. means for displaying an image of the medium comprised of data from the detected relative phase or demodulation of the amplitude modulated diffusional radiation at each detection location.

20. A system for producing images based upon diffusion of intensity modulated radiation and frequency domain analysis as claimed in claim 19, wherein said amplitude modulation of said illuminating means is at a frequency in the megahertz to gegihertz range.

21. A system for producing images based upon diffusion of intensity modulated radiation and frequency domain analysis as claimed in claim 20, wherein said illuminating means includes means for illuminating a patient with near infrared radiation having a wavelength between 600 and 1200 nanometers, amplitude modulating the radiation at a frequency in the megahertz to gegihertz range, and means for displaying internal images of the patient for medical diagnosis.

22. A system for producing images based upon diffusion of intensity modulated radiation and frequency domain analysis as claimed in claim 21, said illuminating means including a laser means for generating near infrared radiation having a wavelength between 680 and 850 nanometers.

23. A system for producing images based upon diffusion of intensity modulated radiation and frequency domain analysis as claimed in claim 21, wherein said illuminating means includes fiber optic cables placed in direct contact with the body of the patient.

24. A system for producing images based upon diffusion of intensity modulated radiation and frequency domain analysis as claimed in claim 23, wherein said detecting means includes fiber optic cables placed in direct contact with the body of the patient.

25. A system for producing images based upon diffusion of intensity modulated radiation and frequency domain analysis as claimed in claim 21, wherein said detecting means includes a camera type detector.

26. A system for producing images based upon diffusion of intensity modulated radiation and frequency domain analysis as claimed in claim 25, including an image intensifier in front of the camera detector, and means for modulating the gain of the image intensifier at a frequency to obtain a heterodyned output frequency for the camera detector of less than 60 hertz.

27. A system for producing images based upon diffusion of intensity modulated radiation and frequency domain analysis as claimed in claim 21, wherein said illuminating means operates below 10 watt power level.

28. A system for producing images based upon diffusion of intensity modulated radiation and frequency domain analysis as claimed in claim 21, further including means for detecting a Doppler frequency shift to measure the flow rate of fluids in the patient.

29. A system for producing images based upon diffusion of intensity modulated radiation and frequency domain analysis as claimed in claim 19, wherein said displaying means includes:
   a. means for displaying a relative phase image of the medium comprised of the detected relative phase values of the diffusional radiation at the plurality of detection locations; and b. means for displaying a demodulation amplitude image of the medium comprised of the detected demodulation amplitudes of the diffusional radiation at the plurality of detection locations.

30. A system for producing images based upon diffusion of intensity modulated radiation and frequency domain analysis as claimed in claim 19, including means for detecting phase and modulation amplitude data at different modulation frequencies and different illumination wavelengths, and a computer programmed to produce false color representations, smoothing, filtering or contrast enhancement.

31. A system for producing images based upon diffusion of intensity modulated radiation and frequency domain analysis as claimed in claim 19, including a memory means for storing in memory the detected phase and modulation amplitude data.

32. A system for producing images based upon diffusion of intensity modulated radiation and frequency domain analysis as claimed in claim 19, wherein said detecting means detects diffusional radiation transmitted by the media.

33. A system for producing images based upon diffusion of intensity modulated radiation and frequency domain analysis as claimed in claim 19, wherein said detecting means detects diffusional radiation reflected by the media.

34. A system for producing images based upon diffusion of intensity modulated radiation and frequency domain analysis as claimed in claim 19, wherein said illuminating means includes a pulsed neutron source.

35. A system for producing images based upon diffusion of intensity modulated radiation and frequency domain analysis as claimed in claim 19, wherein said detecting means comprises a camera and wherein each detection location comprises a pixel of the camera detector.

36. A system for producing images based upon diffusion of intensity modulated radiation and frequency domain analysis as claimed in claim 19, wherein said illuminating means illuminates the media with light which is amplitude modulated.

* * * * *

UNITED STATES PATENT AND TRADEMARK OFFICE
CERTIFICATE OF CORRECTION

PATENT NO. : 5,213,105
DATED : May 25, 1993
INVENTOR(S) : Enrico Gratton, et al.

It is certified that error appears in the above-indentified patent and that said Letters Patent is hereby corrected as shown below:

On the Title Page, Section [56]: "12/1986" should read as --12/1985--

Column 1, line 6: "PR" should read as --RR--

Column 1, line 28: "rear" should read as --near--

Column 1, line 55: "cf" should read as --of--

Column 5, line 51: "at the origin)" should read as --(at the origin)--

Column 6, line 66: "assigning" should read as --assuming--

Column 9, line 50: "ie." should read as --, i.e.,--

Column 12, line 14: "plane" should read as --phase--

UNITED STATES PATENT AND TRADEMARK OFFICE
CERTIFICATE OF CORRECTION

PATENT NO. : 5,213,105
DATED : May 25, 1993
INVENTOR(S) : Enrico Gratton, et. al.

It is certified that error appears in the above-indentified patent and that said Letters Patent is hereby corrected as shown below:

Column 14, line 3: "rot" should read as --not--

Signed and Sealed this

Ninth Day of May, 1995

Attest:

BRUCE LEHMAN

*Attesting Officer*      *Commissioner of Patents and Trademarks*